(12) United States Patent
Pasricha et al.

(10) Patent No.: US 8,326,427 B2
(45) Date of Patent: Dec. 4, 2012

(54) GASTROINTESTINAL ELECTRICAL STIMULATION FOR THE TREATMENT OF PACREATITIS

(75) Inventors: Pankaj Pasricha, Cupertino, CA (US); Jlande Chen, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 68 days.

(21) Appl. No.: 12/836,377

(22) Filed: Jul. 14, 2010

(65) Prior Publication Data
US 2011/0015695 A1 Jan. 20, 2011

Related U.S. Application Data

(63) Continuation-in-part of application No. PCT/US2009/031317, filed on Jan. 16, 2009.

(51) Int. Cl.
*A61N 1/00* (2006.01)
(52) U.S. Cl. .......................................... 607/40
(58) Field of Classification Search .................. 600/104, 600/300; 607/2, 3, 40, 42, 72
See application file for complete search history.

(56) References Cited

U.S. PATENT DOCUMENTS
2006/0287678 A1 * 12/2006 Shafer ............................... 607/2
* cited by examiner

*Primary Examiner* — George Manuel
*Assistant Examiner* — Robert N Wieland

(57) ABSTRACT

A method of preventing acute pancreatitis comprising positioning stimulatory electrodes in the stomach of an individual in need thereof; and administering repetitive trains of short pulse gastrointestinal electrical stimulation effective for suppressing the inflammatory response in the pancreas is provided herein. The electrodes are placed by laproscopic, endoscopic or surgical means. The gastrointestinal stimulation activates vagal reflexes. The activation of the vagal reflexes is via the gastric and pancreatic afferents. The gastrointestinal stimulation also activates the axonal reflexes. The activation of the axonal reflexes is via the dichotomous branches of the spinal nerves. The electrical stimulation is administered concurrently with an endoscopic procedure or immediately following an endoscopic procedure. Also, provided herein is a method of preventing inflammation of a visceral organ comprising positioning a stimulatory electrode in proximity of descending efferents in the vagus, innervating the visceral organ, of an individual in need thereof, and administering repetitive trains of short pulse electrical stimulation effective in activating nicotinic receptors.

17 Claims, 8 Drawing Sheets

GASTROINTESTINAL ELECTRICAL STIMULATION FOR THE TREATMENT OF PACREATITIS

RELATED APPLICATION

This application claims priority to U.S. provisional application No. 61/021,473, filed Jan. 16, 2008. This application also claims priority to PCT/US2009/031317, filed Jan. 16, 2009.

FEDERAL GRANT INFORMATION

The present disclosure was supported by a grant DK-063733-01, from the National Institute of Health. The U.S. Government may have some rights to the disclosure.

BACKGROUND

Acute pancreatitis is a sudden inflammation that occurs over a short period of time. In the majority of cases, acute pancreatitis is caused by gallstones or heavy alcohol use. Other causes include medications, infections, trauma, metabolic disorders, and surgery. In about 10% to 15% of people with acute pancreatitis, the cause is unknown. Endoscopic retrograde cholangiopancreatography (ERCP) has been used for the diagnosis and treatment of pancreatic diseases. This procedure is performed on an outpatient basis under sedation (rarely under general anesthesia). ERCP is associated with a 5%-10% risk of pancreatitis. The risk is increased in those cases where cannulation of the ducts is difficult, the pancreas is normal, or when a sphincterotomy is performed in the setting of sphincter of Oddi dysfunction. A prior history of ERCP-induced pancreatitis is also a risk factor. Other less common risks include bleeding, infection and perforation. Particularly in the setting of pancreatic disease, it is a specialized procedure that should be performed only by experienced endoscopists.

There is a high morbidity and mortality rate for pancreatitis. See Baron, et al, 1999 and Steer et al., 1995. Pharmacologic means of decreasing pancreatic secretion have been attempted with limited success because of the dose-limiting side effects encountered with the drugs, their lack of specificity or their lack of availability. The vagus nerves are strongly implicated in the pathophysiology of pancreatitis. Yoshinaga, et al., 2000. Atropine is a drug that blocks parasympathetic (vagal) nerve endings. It is known to be desirable to use atropine in acute pancreatitis patients to down-regulate pancreatic activity. Unfortunately, for most such patients, this drug cannot be used due to its many side effects.

A need continues to exist for additional feasible and suitable means to treat pancreatitis. Likewise, a need continues to exist for additional feasible and suitable means to treat other gastrointestinal tract disorders.

SUMMARY

Provided herein is a method of preventing acute pancreatitis comprising positioning stimulatory electrodes in the stomach of an individual in need thereof; and administering repetitive trains of short pulse gastrointestinal electrical stimulation effective for suppressing the inflammatory response in the pancreas.

Also, provided herein is a method of preventing acute pancreatitis comprising positioning a stimulatory electrode in the stomach, in proximity of a dichotomously branched spinal nerve innervating the stomach and the pancreas, of an individual in need thereof, and administering repetitive trains of short pulse electrical stimulation effective, at least in part in, blocking the pro-inflammatory spinal reflexes.

Further, provided is a method of preventing inflammation of a visceral organ comprising positioning a stimulatory electrode in proximity of descending efferents in the vagus, innervating the visceral organ, of an individual in need thereof, and administering repetitive trains of short pulse electrical stimulation effective in activating nicotinic receptors.

More specifically, the disclosure provides a method of preventing acute pancreatitis in a subject comprising: positioning stimulatory electrodes in the peritoneal cavity of the subject and administering repetitive trains of short pulse gastric electrical stimulation effective for suppressing the inflammatory response in the pancreas.

In certain aspects, the method may be used when acute pancreatitis develops due to an endoscopic procedure. Optionally, the endoscopic procedure selected from the group consisting of Endoscopic retrograde cholangiopancreatography (ERCP), and endoscopic sphincterotomy.

In certain aspects of the disclosure the method of administering repetitive trains of short pulse gastric electrical stimulation may include trains of pulses are set on for a range of period between about 0.1 seconds to less than or equal to 5 seconds and set off for a range of period between about 0 to less than or equal to 10 minutes. Optionally the methods include repetitive trains of pulses administered in the range between about 1Hz. to less than or equal to 150 Hz. Optionally, the methods may include repetitive trains of pulses have a pulse width in the range between about 0.1 ms to less than or equal to 2.0 ms. Optionally the methods may include repetitive trains of pulses have an amplitude in the range between about 0.1 mA to less than or equal to 20.0 mA.

In certain aspects of the disclosure the methods described above may further include placing the electrodes by laproscopic, endoscopic or surgical means.

In certain aspects of the disclosure, in methods involving gastrointestinal stimulation, such stimulation may activate vagal reflexes. Optionally, activation of the vagal reflexes is via the gastric and pancreatic afferents. Optionally in methods involving gastrointestinal stimulation, the stimulation activates the axonal reflexes. Optionally, activation of the axonal reflexes is via the dichotomous branches of the spinal nerves innervating the stomach and the pancreas.

In certain aspects of the disclosure pertaining to the methods described above, electrical stimulation is administered concurrently with an endoscopic procedure. Optionally or alternatively, in certain aspects of the disclosure pertaining to the methods described above, electrical stimulation is administered following an endoscopic procedure.

Certain aspects of the disclosure pertain to a method of preventing acute pancreatitis in a subject comprising: positioning a stimulatory electrode in the peritoneal cavity, in proximity of a dichotomously branched spinal nerve innervating the stomach and the pancreas, of an individual in need thereof, and administering repetitive trains of short pulse electrical stimulation effective, at least in part in, blocking the pro-inflammatory spinal reflexes.

Optionally, in the method described above repetitive trains of pulses are set on for a range of period between about 0.1 seconds to less than or equal to 5 seconds and set off for a range of period between about 0 to less than or equal to 10 minutes. Optionally, the repetitive trains of pulses are administered in the range between about 1Hz. to less than or equal to 150 Hz. Optionally, the repetitive trains of pulses have a pulse width in the range between about 0.1 ms to less than or equal to 2.0 ms. Optionally, the repetitive trains of pulses have an amplitude in the range between about 0.1 mA to less than or equal to 20.0 mA.

In certain aspects of the method described above electrodes are placed by laproscopic, endoscopic or surgical means. Optionally the electrodes are stimulatory electrodes and are placed in the stomach, small intestines, colon or anorectum.

Certain aspects of the disclosure pertain to a method of preventing inflammation of a visceral organ comprising positioning a stimulatory electrode in proximity of descending efferents in the vagus, innervating the visceral organ and administering repetitive trains of short pulse electrical stimulation effective in activating nicotinic receptors.

Certain aspects of the disclosure pertain to a method of preventing acute pancreatitis in a subject comprising: positioning stimulatory electrodes in the peritoneal cavity of the subject and administering repetitive trains of short pulse gastric electrical stimulation effective for suppressing the inflammatory response in the pancreas.

Certain aspects of the disclosure pertain to a method of preventing acute pancreatitis in a subject comprising: positioning a stimulatory electrode in the peritoneal cavity, in proximity of a dichotomously branched spinal nerve innervating the stomach and the pancreas, of an individual in need thereof, and administering repetitive trains of short pulse electrical stimulation effective, at least in part in, blocking the pro-inflammatory spinal reflexes.

Certain aspects of the disclosure pertain to a method of preventing inflammation of a visceral organ comprising positioning a stimulatory electrode in proximity of descending efferents in the vagus, innervating the visceral organ and administering repetitive trains of short pulse electrical stimulation effective in activating nicotinic receptors.

The details of one or more embodiments of the disclosure are set forth in the accompanying drawings and the description below. Other features, objects, and advantages of the disclosure will be apparent from the description and drawings, and from the claims.

BRIEF DESCRIPTION OF THE DRAWINGS

In order that the manner in which the above recited and other enhancements and objects of the disclosure are obtained, a more particular description of the disclosure briefly described above will be rendered by reference to specific embodiments thereof, which are illustrated, in the appended drawings. Understanding that these drawings depict only typical embodiments of the disclosure and are therefore not to be considered limiting of its scope, the disclosure will be described with additional specificity and detail through the use of the accompanying drawings in which:

FIG. 7C shows bridged insertion needles.

Figure 1A:
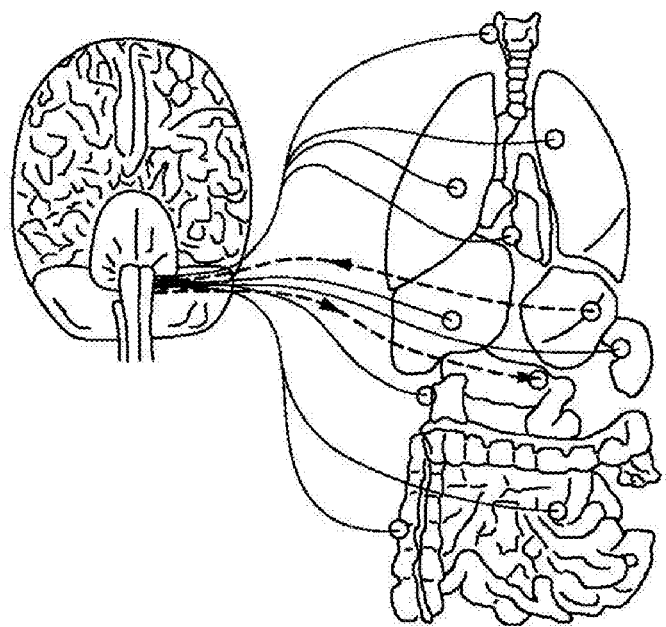
FIGS. 1A-1B illustrate two pathways by which electrical stimulation of the peritoneal cavity can modulate inflammation in the pancreas: the vagal reflex carried by gastric vagal afferents and pancreatic vagal efferents (FIG. 1A) and/or axonal reflex within a dichotomous single nerve innervating both the stomach and the pancreas (FIG. 1B).
Figure 1B:
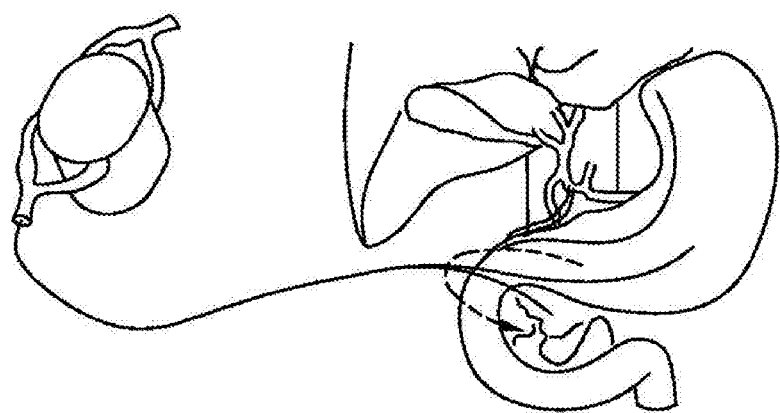

LIST OF REFERENCE NUMERALS 1 electrode lead with an insertion axis
2 needle
3 hollow bore
4 entrance tip
5 first or a single pair of radially spaced arms
6 second or additional pair of radially spaced arms
7 bridge
8 skin
9 panniculus
10 gastrointestinal wall
11 guide rod
12 skin bolster
13 gastric bolster
14 plurality of electric leads
15 lead ends
16 conductive wire
17 second needle

DETAILED DESCRIPTION OF THE DISCLOSURE

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings and/or examples making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition.

As used herein, all percentages are percentages by weight, unless stated otherwise.

As used herein, the "gastrointestinal tract" (GI tract) in certain instances may refer to the "gut" or the "alimentary canal" that is a continuous, coiled, hollow, muscular tube that winds through the ventral body cavity. It is open to the external environment at both ends. In a human, its organs (gastrointestinal organs) generally include the mouth, pharynx, esophagus, stomach, small intestine (duodenum, jejunum, and ileum), and large intestine (cecum, appendix, colon, rectum, and anal canal). The large intestine leads to the terminal opening, or anus.

The "gastrointestinal wall" in certain instances may refer to the continuous, coiled, hollow, muscular tube that is the gastrointestinal tract. The wall generally defines the center (lumen) of the GI tract (the hollow portion of the tube). The wall has a thickness defining an interior wall adjacent to the center of the GI tract and an exterior wall.

As used herein, "gastrointestinal action" in certain instances may refer to any GI actions. Thus, gastrointestinal action includes, for example, gastrointestinal electrical activity, gastrointestinal contractile activity (such as stomach contractile activity), gastrointestinal motility, gastric emptying, gastrointestinal pressure, gastrointestinal impedance, and afferent nerve activity (including vagal nerve, sympathetic nerves, and spinal nerves).

A subject in certain instances may refer to an animal, including a human, subject. For non-human animal subjects, the particular structure of the GI tract may differ from that of a human. For such non-human animal subjects, the gastrointestinal tract, as used herein, refers to that non-human animal's known GI tract and GI organs. It is understood that the first step of the present disclosure includes selecting a subject which would benefit from the method of the subject, such as, for example, selecting a subject who is suffering from gastrointestinal pain.

An "optimum level" in certain instances may refer to a pre-determined target, which is determined based on the desired outcome. For example, in GES (see below), the definition of optimization is based on an optimal combination of efficacy, safety and feasibility. That is, the optimal GES settings are those that result in a significant reduction in pain (efficacy) but do not induce undesired symptoms, such as nausea or vomiting (safety) with minimal energy (maximally feasible for an implantable device). Iterative adjustments of stimulation parameters are made to achieve this result. For any particular gastrointestinal action, an "optimum level" or desirable level can be determined by monitoring the appropriate GI action. As another example, an appropriate amount of GI pressure at the esophageal sphincter can be determined which prevents reflex of stomach juices into the esophagus, while still allowing the passage of food items into the stomach. With this predetermined "optimum level", a stimulatory electrode can be established with a sensor to maintain this optimum level. The optimum level is thus fact and subject specific, but readily determinable with routine experimentation, taking into account the goal of an optimal combination of efficacy, safety and feasibility.

A "stimulatory electrode" in certain instances may refer to a conductor of electricity through which current enters a medium (a subject), whereas a "sensor" refers to a conductor of electricity through which current leaves a medium (a subject). Typically, for gastrointestinal uses, the stimulatory electrodes and sensors are constructed of teflon-insulated wires such as are used for cardiac pacing wires. The stimulatory electrode is electrically connected (i.e., conductively connected) to a source of electrical current (often referred to as a pacemaker where a set pattern of electrical current is delivered), and the sensor is electrically connected to a device for determining the level of electrical current "sensed" by the sensor (an electrical recorder, for example). The stimulatory electrode is thus used to "generate" electrical current and the sensor is thus used to "detect" electrical current. Note that the stimulatory electrode can be used to "generate" electrical current, which is itself a defined "gastrointestinal action", but the generation of electrical current can also produce other gastrointestinal actions (such as, for example, stomach contraction or esophageal pressure). The language "generating" GI action is thus intended to cover both concepts, i.e. the generation of the initial electrical current and the ultimate gastrointestinal action which is "generated" as a result of the current (i.e. the contraction or pressure).

"Operatively connected" in certain instances may refer to the connection between the stimulatory electrode and the sensor, and indicates that the operation of one is connected to the operation of the other. In particular, the sensor connects to a device which determines the level of electrical current sensed by the sensor. A representation of that level is then fed to the source of electrical current that is electrically connected to the stimulatory electrode. The source of electrical current is provided with a programmable computer circuit that enables the level from the sensor to determine, or dictate, the operation of the source (i.e., electrical current is generated by the source and fed through the stimulatory electrode in response to and an in relation to the amount of the level of electrical activity sensed by the sensor). Thus, the "operatively connected" stimulatory electrode and sensor enable the retrograde feedback concept to occur.

"Positioning" a stimulatory electrode or a sensor in certain instances may refer to placement of the stimulatory electrode or sensor on or in a subject. Placement or positioning of stimulatory electrodes can be accomplished by laproscopic, endoscopic or surgical means. In general, laparoscopic placement of electrodes is performed by inserting a scope through one trocar or sheath and the electrode through one or more other trocars or sheaths. The trocars are sleeves which are inserted through a body opening which may be a surgically made opening or portal through the skin, muscle and peritoneal membrane. The trocar typically has an inside diameter of 10 millimeters. Often the body cavity, such as the abdominal peritoneal area is inflated with low pressure carbon dioxide. An insufflation pressure of about 12 millimeters of HG or less is maintained during the operation by a sealing membrane located in the trocar opening comprising a thin rubber material having a small diameter hole of approximately 3 millimeters therein. The electrodes are inserted through the membrane hole which stretches to accommodate the larger size thereby forming and effective seal Endoscopic placement of the electrodes can be accomplished by either using the endoscope for both visualization as well as insertion of electrodes or by endoscopic visualization to guide insertion of the electrodes. For the latter method, the conscious patient is sedated and an endoscope is inserted into the stomach via the mouth. Then, a sharp, long and small needle with a hole in the middle (similar to needles used for the placement of percutaneous endoscopic gastronomy tubes) is inserted into the stomach by puncturing the skin. A teflon-insulated wire, peeled off at the distal portion, is then extended, under endoscopic observation, into the stomach via the hole of the needle. The exposed, peeled off portion of the inserted teflon-insulated wire serves as an electrode. The needle is removed after the insertion of the wire. The wire has an engaging means. The engaging means allow for engagement of the wire with the mucosa, when the wire is slowly pulled from the exterior, and stops it from being further pulled out. On the external end the wire is attached to the abdominal skin and protected from infection.

The engaging means for the electrode refers to any suitable means that would allow for the successful engagement of the electrodes to the mucosa. These include but are not limited to barbs, expandable hooks, and suction based fasteners arranged at the distal tip of the electrodes.

"Periodically" in certain instances may refer to evenly or unevenly spaced time intervals.

"Differs from" in certain instances may refer to a statistically significant variation between two compared values, and therefore does not always require a difference in orders of magnitude. It should be apparent that where small values are compared, statistically significant variations can likewise be very small, and where large values are compared, statistically significant variations can be large. Conversely, "substantially equals" refers to a statistically insignificant variation between two compared values.

"Electrical field stimulation" in certain instances may refer to the generation of an "electrical field", which indicates that the area of distribution of the electrical current from the stimulation encompasses the entire area between and/or surrounding two or more stimulatory electrodes, and "field" is used to imply that the two or more stimulatory electrodes are positioned at least about three centimeters apart (thus the term "field" to differ from prior stimulations where the two electrodes of a pair are positioned in close proximity to one another and do not generate a "field").

A "device" in certain instances may refer to any suitable item which can readily be and is desirable to be placed in the GI tract. Such devices can include, for example, stimulatory electrodes and sensors for use in the GES method of the subject disclosure. Such devices could also include a small balloon to be used to provide pressure within the esophagus or small/large intestine. A small gauge for measurement of pressure could be a device in accordance with the subject disclosure.

Electrical stimulation refers to an electrical signal, which includes a train of pulses. A train of pulses refers to a method in which the stimulus is composed of repetitive trains of short pulses derived from a combination of two signals, a) a continuous short pulse with high frequency (in the order of 5 to 150 Hz), and b) control signal to turn the pulses on or off, such as "X" seconds on and "Y" seconds off. The addition of "X" and "Y" then determines the frequency of the pulse train. A frequency approximately equal to the physiologic frequency of stimulation will be performed using trains of pulses. The train will be set on for a period of 0.1 s to 5 seconds and set off for a period of 0 to 10 min. The pulses within a train have a frequency of 5 to 150 Hz width of 0.1 to 2 ms and amplitude of 0.1 mA to 1 OmA or the corresponding voltages that will produce the described current. The methods of providing electrical field stimulation to a gastrointestinal organ are disclosed in WO2001/076690 which is hereby incorporated by reference herein. A discussion of trains of short pulse electrical stimulation is provided in Zhang et al., 2006, which is hereby incorporated by reference herein. Electrical stimulation is also capable from a magnet.

"Long pulse" electrical stimulation in certain instances may refer to an electrical signal which has a long width, such as in the order of from about 1 to about 900 milliseconds, or about 2 to about 600 milliseconds, and has a frequency approximately equal to the physiologic frequency of the gastric slow wave of the subject. For example, the long pulse electrical stimulation has a frequency of about ±20%, or about ±10%, of the physiologic frequency of the gastric slow wave of the subject.

"Short pulse" electrical stimulation in certain instances may refer to an electrical signal which has a short width, such as in an order of from about 50 to about 999 microseconds, or about 100 to about 300 microseconds and having a frequency from about 5 Hz to about 500 Hz. The number of short pulses applied range from 1 to about 50.

Synchronization or synchronized in certain instances may refer to applying the long pulse and/or short pulse electrical stimulation substantially concurrently with the occurrence of the gastric slow wave of the subject.

Electrical stimulation of the gastrointestinal tract has been proposed to treat motility related disorders and other gastrointestinal diseases. The electrical stimulation has been proposed in a number of forms, such as, e.g., pacing, electrical contractile stimulation or other stimulation, e.g., to treat nausea or obesity. Electrical pacing of the gastrointestinal tract is generally defined as a periodic electrical stimulation that captures and/or controls the frequency of the pacesetter potential or slow wave activity of the intestinal organ (including in a retrograde direction). Electrical contractile stimulation generally refers to stimulation that directly causes or results in muscular contraction associated with the gastrointestinal tract. There have been a number of reports on Gastric electrical stimulation for the treatment of gastrointestinal motility disorders in both dogs and humans (U.S. Pat. Nos. 5,423,872, 5,690,691, and 5,836,994; PCT International Publication No. WO 99/30776; Bellahsene et al. 1992; Mintchev et al. 1998; Mintchev et al. 1999; Mintchev et al. 2000; Chen et al. 1998; Chen et al. 1995). These disorders are characterized by poor contractility and delayed emptying and the aim of electrical stimulation in this setting is to normalize the underlying electrical rhythm and improve these parameters. Gastric emptying plays an important role in regulating food intake. Several studies have shown that gastric distention acts as a satiety signal to inhibit food intake (Phillips and Powley 1996) and rapid gastric emptying is closely related to overeating and obesity (Duggan and Booth 1986). Obese subjects have a more rapid emptying rate than non-obese subjects (Wright et al. 1983). In general, this is done by antegrade or forward gastric (or intestinal) stimulation. Previous work on antegrade gastrointestinal stimulation has been focused on its effects on gastric myoelectrical activity, gastric motility, and gastric emptying, (Lin et al. 1998; Eagon and Kelly 1993; Hocking et al. 1992; Lin et al. 2000; McCallum et al. 1998; Miedema et al. 1992; Qian et al. 1999; Abo et al. 2000; Bellahsene et al. 1992). Gastrointestinal electrical stimulation, as used in the present disclosure, alters sympathetic nerves, such as the spinal afferent neurons.

Pancreatitis is a severe disease that is associated with high morbidity and mortality. It is typically caused by alcohol abuse or gallstones and most patients suffering from pancreatitis require hospitalization. Acute pancreatitis is a major and potentially serious complication of Endoscopic retrograde cholangiopancreatography (ERCP) and endoscopic sphincterotomy, occurring at a frequency ranging from 1-10%. Although, the exact pathogenesis of ERCP induced pancreatitis is unknown it may involve activation of pancreatic enzymes, vascular impairment, activation of clotting, kinin and arachidonic acid pathways and recruitment of inflammatory cells. These events lead to a self-sustaining casade of parenchymal cell injury of pancreas. No therapies are available to treat the illness; only palliative care is available.

Current research has implicated the inflammatory response as playing a critical role in the development of pancreatitis. Inflammation results from the up-regulation of a multitude of pro-inflammatory signaling molecules including TNF-$\alpha$, IL-6, IL-8 and others. Activation of the inflammatory pathway in the pancreas is thought to damage pancreatic tissue, thereby leading to the disease. Inflammation in any tissue requires communication across many systems including immune, endocrine and nervous systems. Information from the pancreas, like other visceral organs, is conveyed to the central nervous system principally via two pathways—the spinal afferents that generally convey painful stimuli and the vagus afferents that carry non-painful and physiological stimuli. Cytokines and other inflammatory factors can activate these pathways and initiate multiple responses including fever and other acute phase reflexes. In addition an anti-inflammatory reflex, the nicotinic anti-inflammatory pathway," is initiated that involves descending efferents in the vagus and dampens the macrophage response by activation of specific nicotinic receptors on these cells.

Traditionally, this pathway is considered a classical vagal reflex, although alternatively, an axon reflex utilizing cholinergic vagal afferents might be implicated.

The vagus nerve plays an important role in the parasympathetic antiinflammatory pathway. The nervous system, through the vagus nerve, controls inflammation by decreasing the release of TNF-α from endotoxin stimulated macrophages. This anti-inflammatory effect is mediated by an interaction of acetylcholine, the principal vagal neurotransmitter, with macrophage cholinergic nicotinic receptors expressing the α7 subunit. In fact, a specific blocker of parasympathetic (vagus nerves) control of secretion demonstrated a shortened recovery period in patients with acute pancreatitis. See Zapater, et al., 2000; Norton, et al., 2001. However, most of these drugs cannot be used routinely due to many side effects.

By contrast to vagal afferents, spinal afferents are generally thought to actually promote inflammation via local releases of substances such as SP and CGRP. A single spinal nerve is capable of innervating both the stomach and the pancreas by diverging at its terminal into separate fibers. Thus, the dichotomous spinal innervation of the stomach and the pancreas, enables electrical stimulation of the stomach to mediate inhibition of the proinflammatory reflexes that serves to cause inflammation of the pancreas. Hence, electrical stimulation of the stomach could modulate inflammation of the pancreas via two potential pathways: 1) activation of anti-inflammatory vagal reflexes involving gastric afferents and pancreatic efferents and/or 2) suppression of pro-inflammatory axonal reflexes involving the dichotomous branches of the spinal nerves and/or 3) activation of other anti-inflammatory neural pathways between the stomach and pancreas.

Thus, disclosed herein is a method of preventing acute pancreatitis in a subject comprising positioning stimulatory electrodes in the peritoneal cavity of the subject and administering repetitive trains of short pulse gastrointestinal electrical stimulation effective for suppressing the inflammatory response in the pancreas. Specifically, in various embodiments, the acute pancreatitis develops due to an endoscopic procedure. In general, in various embodiments, the endoscopic procedure is selected from the group consisting of Endoscopic retrograde cholangiopancreatography (ERCP), and endoscopic sphincterotomy. Moreover, the repetitive trains of pulses are set on for a range of period between about 0.1 seconds to less than or equal to 5 seconds and set off for a range of period between about 0 to less than or equal to 10 minutes. Further, the repetitive trains of pulses are administered in the range between about IHz. to less than or equal to 150 Hz, a pulse width in the range between about 0.1 ms to less than or equal to 2.0 ms, and an amplitude in the range between about 0.1 mA to less than or equal to 20.0 mA. Additionally, the electrodes are placed by laproscopic, endoscopic or surgical means. Specifically, the gastrointestinal stimulation activates vagal reflexes. Moreover, the activation of the vagal reflexes is via the gastric and pancreatic afferents. Additionally, the gastrointestinal stimulation activates the axonal reflexes. Further, the activation of the axonal reflexes is via the dichotomous branches of the spinal nerves innervating the stomach and the pancreas. In general, the electrical stimulation is administered concurrently with an endoscopic procedure. Additionally, the electrical stimulation is administered following an endoscopic procedure.

Further, disclosed is a method of preventing acute pancreatitis in a subject comprising positioning a stimulatory electrode in the peritoneal cavity, in proximity of a dichotomously branched spinal nerve innervating the stomach and the pancreas, of an individual in need thereof, and administering repetitive trains of short pulse electrical stimulation effective, at least in part in, blocking the pro-inflammatory spinal reflexes. Specifically, the acute pancreatitis is due to an endoscopic procedure. In general, the electrical stimulation is administered concurrently with an endoscopic procedure. Additionally, the electrical stimulation is administered following an endoscopic procedure. In various embodiments, the electrodes are placed in the stomach.

Also, disclosed herein is a method of preventing inflammation of a visceral organ comprising positioning a stimulatory electrode in proximity of descending efferents in the vagus, innervating the visceral organ, of an individual in need thereof, and administering repetitive trains of short pulse electrical stimulation effective in activating nicotinic receptors. In general, the stimulatory electrodes are placed in the stomach, small intestines, colon or anorectum.

The disclosures described above may further concern positioning one or more electrodes, such as stimulatory electrodes, relative to the subject so that the electrode can generate electrical stimulation effective in activating nicotinic receptors or to block pro-inflammatory spinal reflexes or for electrical stimulation effective for suppressing the inflammatory response in the pancreas or electrical stimulation of the stomach in order to modulate inflammation of the pancreas via 1) activation of anti-inflammatory vagal reflexes involving gastric afferents and pancreatic efferents and/or 2) suppression of pro-inflammatory axonal reflexes involving the dichotomous branches of the spinal nerves and/or 3) activation of other anti-inflammatory neural pathways between the stomach and pancreas.

Optionally the methods above may additionally include positioning a sensor relative to the subject so that the sensor senses the level of total electrical stimulation. In certain aspects, the sensor may be operatively connected to the electrode. Optionally, the method may include periodically detecting the level of electrical stimulation with the sensor. Still further, the method may include periodically generating non-naturally occurring electrical stimulation with the electrode.

Certain aspects of the disclosure concern methods of providing electrical field stimulation to a gastrointestinal organ or the pancreas. Such a method may comprise positioning a first electrode in a gastrointestinal organ and/or pancreas and positioning a second electrode in the gastrointestinal organ or pancreas. The electrodes may be stimulatory electrodes. Optionally, the electrodes may be spaced apart from one another. Optionally, the second electrode may be placed 1, 2, 3, 4, 5, 6, 7, 8, 9 or 10 mm or 20, 30, 40, 50, 60, 70, 80, 90 mm or 1, 2, 3, 4, 5, 6, 7, 8, 9 or 10 cm or some range therein from the first electrode. In certain cases, the second electrode may be preferably placed at least about two centimeters from the first electrode. Optionally, the method may further comprise electrically stimulating the gastrointestinal organ and/or pancreas simultaneously through the first and the second stimulatory-electrodes, wherein one of the first and the second stimulatory electrodes has a positive polarity and wherein the other one of the first and the second stimulatory electrodes has a negative polarity, thereby providing electrical field stimulation to the gastrointestinal organ and/or pancreas between the first and the second stimulatory electrodes.

Certain aspects of the disclosure concern methods of providing electrical potential gradient in a gastrointestinal organ and/or pancreas. Such a method may comprise positioning a first electrode in a gastrointestinal organ and/or pancreas; positioning a second stimulatory electrode in the gastrointestinal organ and/or pancreas. The electrodes may be stimulatory electrodes. Optionally, such a method further comprises the second electrode being positioned at a distance from the first electrode. Optionally, the second electrode may be placed 1, 2, 3, 4, 5, 6, 7, 8, 9 or 10 mm or 20, 30, 40, 50, 60, 70, 80, 90 mm or 1, 2, 3, 4, 5, 6, 7, 8, 9 or 10 cm or some range therein from the first electrode. In certain cases, the second electrode may be preferably placed at least about two centimeters from the first electrode. Optionally the method further comprises electrically stimulating the gastrointestinal organ and/or pancreas simultaneously through the first and the second stimulatory electrodes. Preferably in such a method, voltage generated by the first electrode differs from voltage generated by the second electrode. Such a method may result in the providing of an electrical potential gradient in the gastrointestinal organ and/or pancreas between the first and the second electrodes.

Certain aspects of the disclosure provide methods of treatment by positioning a plurality of electrodes in a gastrointestinal organ and/or pancreas. Such a method may comprise positioning a first pair of bipolar stimulatory electrodes in contact with a gastrointestinal organ and/or pancreas. Optionally the placement is along the afferent vagus neural pathway. Optionally, such a method further comprises positioning a second pair of bipolar stimulatory electrodes in contact with a gastrointestinal organ and/or pancreas along the afferent vagus neural pathway. Optionally, when the use of two pairs of electrodes is contemplated, such a method further comprises administering a phased pulse regimentation of the electrical stimulation which progresses from the first pair of electrodes to the second pair of electrodes. Such a method may comprise placement of the electrodes by laproscopic, endoscopic or surgical procedures, through the bore of a needle or some combination thereof. Such a method may further comprise electrical stimulation in repetitive pulse trains.

Certain aspects of the disclosure provide methods of placing a device in or through a gastrointestinal organ and/or pancreas of a subject. Such a method may comprise placing the device from the exterior of the subject. Optionally, such a method further comprises inserting at least part of a needle, such as an end of a needle, from the exterior of a subject into the gastrointestinal tract of the subject. Optionally, such a method further comprises a needle having an interior bore. In such a method, wherein insertion into a gastrointestinal organ is contemplated the gastrointestinal tract of the subject may be considered to have center defined by a wall. The wall of the gastrointestinal tract may be considered to have a thickness defining an interior wall adjacent to the center and an exterior wall. The method may further comprise inserting a needle, such as a needle having an interior bore, through the wall of the gastrointestinal tract and into the center of the gastrointestinal tract. Optionally or alternatively, wherein placement of a device into the pancreas of a subject is contemplated, the method may comprise inserting a needle, such as a needle having an interior bore, into the pancreas. The method may further comprise inserting a device through the interior bore of the needle. Optionally, the method contemplates that they device may have engaging means to engage the thickness of the wall of a gastrointestinal organ of the gastrointestinal tract or to engage the thickness of the pancreas. In methods wherein a needle with an interior bore and a device with an interior wall engaging means is contemplated, the method may further comprise inserting the device at least until the interior wall engaging means extends beyond the interior bore of the needle. Optionally, such a method further comprises removing the needle. Optionally, such a method further comprises retracting the device until the interior wall engaging means engages the interior wall of the gastrointestinal tract of a gastrointestinal organ of the subject. Alternatively, such a method further comprises retracting the device until the interior wall engaging means engages the thickness of a gastrointestinal organ or the thickness of the pancreas.

The methods of placing a device described above may optionally further comprise inserting at least part of a needle, such as an end of a needle, from the exterior of a subject into the gastrointestinal tract of the subject or into the thickness of a gastrointestinal organ of a subject or into the thickness of the pancreas of a subject. Optionally, such a method further comprises a needle having an interior bore. In such a method, the gastrointestinal organ may be considered to have a thickness. Likewise, in such a method the pancreas may be considered to have a thickness. In the case of a gastrointestinal organ, the gastrointestinal tract of the subject may be considered to have center defined by a wall. The wall of the gastrointestinal tract may be considered to have a thickness defining an interior wall adjacent to the center and an exterior wall. In either a gastrointestinal organ or a pancreas having a thickness, the method may further comprise inserting a needle, such as a needle having an interior bore, into the thickness of the gastrointestinal organ or into the thickness of the pancreas. Optionally, in such a method the needle may be inserted until the end of the needle is positioned in the thickness of the wall between the interior wall and the exterior wall. The method may further comprise inserting a device through the interior bore of the needle. Optionally, in such a method, the device may have an engaging means. Optionally, such a method further comprises inserting the device until the engaging means extends beyond the interior bore of the needle into the thickness of the gastrointestinal organ or the pancreas. Optionally, such a method further comprises removing the needle. Optionally, such a method further comprises retracting the device. Optionally, such a method further comprises retracting the device until the engaging means engages the thickness. Such a method may thereby place the device in the gastrointestinal wall of the subject or in the pancreas of a subject. Optionally the device may comprise an electrode, such as a stimulatory electrode. Optionally the device may comprise a sensor such as an electrical sensor. Optionally the device may comprise both an electrode and a sensor. Optionally, the device may comprise a plurality of electrodes. Optionally the device may comprise a plurality of sensors. Optionally the device may comprise a plurality of electrodes and one sensor. Optionally the device may comprise a plurality of sensors and one electrode. Optionally the device may comprise a plurality of electrodes and sensors.

Certain aspects of the disclosure provide methods of endoscopic placement or visualization of one or more electrode and/or sensor. Such a method can comprise using an endoscope for a variety of applications such as but not limited to: 1) visualization and insertion of electrodes and/or sensors with an endoscope 2) endoscopic visualization to guide insertion of the electrodes and/or sensors, 3) endoscopic insertion of electrodes and/or sensors wherein the observation of the placement is done with a colonoscope or laproscopically and 4) using a plurality of endoscopes for placement of electrodes or sensors (e.g. one endoscope to observe placement of an electrode and another endoscope to place the electrode and/or sensor). Optionally such a method may comprise the use of a single electrode and a single sensor or a plurality of electrodes and sensors or some combination thereof. Optionally, such methods further consist of a subject being sedated prior to or during the endoscopic visualization or placement of the electrode. Optionally, such methods further consist of inserting an endoscope or endoscopes in the gastrointestinal tract via the mouth. Optionally, in methods wherein observation of the placement of one or more electrode and/or sensor is contemplated, the methods may further comprise the insertion of a needle into the gastrointestinal tract from the exterior of the subject. Optionally, the methods further comprise a needle penetrating the gastrointestinal tract to the interior of the gastrointestinal tract or to the thickness of the wall of the gastrointestinal tract. In methods wherein a needle is contemplated, the needle may be a hollow needle with a hole in the middle such as a needle having a hollow interior bore. In other methods, a laproscope or trocar is contemplated to access the exterior of the gastrointestinal tract or the pancreas.

Certain aspects of the disclosure provide methods of colonoscopic placement or visualization of one or more electrode and/or sensor. Such a method can comprise using an colonoscope for a variety of applications such as but not limited to: 1) visualization and insertion of electrodes and/or sensors with a colonoscope 2) colonoscopic visualization to guide insertion of the electrodes and/or sensors, 3) colonoscopic insertion of electrodes and/or sensors wherein the observation of the placement is done with an endoscope or laproscopically and 4) using a plurality of colonoscopes for placement of electrodes or sensors (e.g. one colonoscope to observe placement of an electrode and another colonoscope to place the electrode and/or sensor). Optionally such a method may comprise the use of a single electrode and a single sensor or a plurality of electrodes and sensors or some combination thereof. Optionally, such methods further consist of a subject being sedated prior to or during the colonoscopic visualization or placement of the electrode. Optionally, such methods further consist of inserting a colonoscope or endoscopes in the gastrointestinal tract via the mouth. Optionally, in methods wherein observation of the placement of one or more electrode and/or sensor is contemplated, the methods may further comprise the insertion of a needle into the gastrointestinal tract from the exterior of the subject. Optionally, the methods further comprise a needle penetrating the gastrointestinal tract to the interior of the gastrointestinal tract or to the thickness of the wall of the gastrointestinal tract. In methods wherein a needle is contemplated, the needle may be a hollow needle with a hole in the middle such as a needle having an hollow interior bore. In other methods, a laproscope or trocar is contemplated to access the exterior of the gastrointestinal tract or the pancreas.

Certain aspects of the disclosure wherein placement of a device endoscopically through the esophagus and into a gastrointestinal organ is contemplated, the device may be implanted in the interior wall of the gastrointestinal tract. Optionally, the method comprises preparing an opening in the gastrointestinal tract from the interior wall of the gastrointestinal tract to access the wall of the gastrointestinal tract for implanting the device. Optionally, the method comprises creating a cavity in the wall of the gastrointestinal tract. Optionally, the method further comprises placing the device through the opening into the wall of the gastrointestinal tract. Optionally, the method further comprises closing the cavity. According to one variation, after preparing the opening in gastrointestinal tract, a pocket or cavity is prepared in the gastrointestinal tract to receive the device. Optionally, a knife, needle or cutting instrument may be used to prepare an opening in the wall of the gastrointestinal tract. Optionally, such a method further comprises injecting a material or solution into the opening for implanting the device, to form a bleb or blister in the gastrointestinal wall. Optionally, such a method may comprise the use of a tissue dissector to prepare a cavity. Optionally, the tissue dissector may be a blunt dissector, for example, a blunt tool, an expandable compliant or non-compliant balloon, or another mechanically expanding device, or a cutting blade. The dissector may also be a device using an energy source to break down or cut tissue such as an electrosurgical cutting or coagulating device, or an ultrasonic or laser device.

In certain aspects of the disclosure wherein placement of a device is contemplated, a device may comprise a Teflon™-insulated wire may be extended via the hole of the needle. Optionally the insulated wire may be peeled off at the distal portion. Optionally, the exposed or peeled off portion of the inserted Teflon™-insulated wire serves as an electrode. In methods where insertion of a needle is contemplated, the needle may be removed after the insertion of the wire. In methods where a wire is contemplated, the wire may further comprise an engaging means. The engaging means may allow for engagement of the wire with the interior wall of the gastrointestinal tract or the thickness of the wall of a gastrointestinal organ of the gastrointestinal tract or the pancreas when the wire is pulled from the exterior. Such an engaging means may prevent the wire from being further pulled out of the interior of the gastrointestinal tract or the wall of a gastrointestinal organ of the gastrointestinal tract or the pancreas.

Certain aspects of the disclosure contemplate the placement of a device. As will be apparent, the device may comprise an electrode or a sensor or a plurality of electrodes and sensors or a single electrode and a plurality of sensors or a plurality of electrodes and a single sensor.

In certain aspects of the disclosure wherein a device is contemplated, the device may comprise an engaging means wherein the engaging means itself comprises a plurality of radially extendable arms positioned at an axis perpendicular, acute or obtuse to the insertion axis of the stimulator or sensor. The stimulator or sensor is inserted until the axis of the plurality of radially extendable arms extends beyond the interior bore of the needle, at which point the arms radially extend. The electrical stimulator is retracted until the radially extended arms engage the interior wall of the gastrointestinal tract. Optionally, the device may have 2, 3, 4, 5, 6, 7, 8, 9 or 10 radially extendable arms or more. Optionally each radially extendable arm may be positioned to the same angle. Without being limited to the particular example, each radially extendable arm may be positioned perpendicular or 90° from the insertion axis or 120° from the insertion axis or some angle between about 1° and 178° from the insertion axis. Alternatively, each radially extendable arm may be positioned to different angles. Without being limited to the particular example, one radially extendable arm may be positioned at an angle of about 1° from the insertion axis, another radially extendable arm may be positioned at an angle of about 60° from the insertion axis, another radially extendable arm may be positioned at an angle of about 90° from the insertion axis and another radially extendable arm may be positioned at an angle of about 136° from the insertion axis. Optionally, the plurality of radially extendable arms may be in the same plane. Alternatively, one or more radially extendable arms may be in a different plane as compared to another arm or arms. Without being limited to the particular example, two radially extendable arms may be at the terminal end of the device comprising an insertion axis wherein the device is positioned with the terminal end towards the center of the gastrointestinal tract, while three radially extendable arms may be positioned some distance away, such as 2-20 mm from the terminal end of the device along the insertion axis.

In other aspects of the disclosure wherein a device is contemplated, the device may be made of a soft plastic polymer or other medically acceptable non irritating material. Optionally, the device may be compressible. Optionally, the device may further comprise a plurality of electrodes and/or sensors. Optionally the device may be fixed by suture to the gastrointestinal tract. Alternatively, the device may be held stationary with respect to the gastrointestinal tract by a locking mechanism which surrounds wires leading to the stimulators or sensors and may be placed on the exterior wall of the gastrointestinal tract or on the skin of a subject. An example of a device that may be fixed or locked can be found in U.S. Pat. No. 5,292,344.

Certain aspects of the disclosure provide a for a device comprised of biocompatible materials that allow it to remain in the environment of the gastrointestinal tract or within the gastrointestinal tract wall for the life of the device, e.g., several weeks, months or years. Optionally, the electrode(s) or sensor(s) may comprise corrosion resistant metals and alloys such as, e.g. platinum, iridium, gold, tantalum, titanium, stainless steel or alloys of one or more of these metals, e.g., a platinum/iridium alloy. Other non-conductive parts of the device may comprise inert polymers, for example, from the polyolefin family, e.g., HDPE (high density polyethylene), PP (polypropylene), UHMWPE (ultra high molecular weight polyethylene), or fluoropolymer such as PTFE (polytetrafluoroethylene) FEP (fluorinated ethylene propylene) and other members. PMP (polymethylpentene), polysulfone, PMMA (polymethylmethacrylate) may also be used. Softer materials may be used, such as, e.g., silicones, C-Flex, polyurethanes, co-polymer nylons (e.g. PEBAX).

In other aspects of the disclosure wherein a device is contemplated, the device may comprise one or more stimulators and/or electrodes. Optionally such a device may further comprise a first and second pair of attachment members that secure the device in the gastrointestinal tract wall. Optionally, the first attachment members of the device are the first to enter the gastrointestinal tract wall. In such a device the attachment members may comprise a flexible material. Optionally the attachment members may be considered tines. Optionally the first tines may be considered leading tines that define an obtuse angle with respect to travel of the insertion axis of the device. Optionally, the leading tines have a diameter of about 1 mm and a length of about 3 mm. Optionally the second tines may define an angle which is obtuse, perpendicular or acute with respect to travel of the insertion axis of the device. Optionally, wherein the second tines are at an obtuse angle with respect to travel of the insertion axis of the device, the second pair of tines may or may not penetrate the gastrointestinal organ or pancreas. Alternatively, wherein the second tines are at an acute or perpendicular angle with respect to travel of the insertion axis of the device, the second pair of tines may not penetrate the gastrointestinal tract wall. Examples of a device of this type may be found in U.S. Pat. No. 6,542,776. Such a device may be inserted into or through a gastrointestinal organ or into the pancreas through a trocar from the exterior of the subject. Alternatively, such a device may be inserted from the exterior of a subject through a needle with a hollow bore wherein the flexible tines are compressed to be at an obtuse angle during insertion through the needle and into the wall of a gastrointestinal organ or pancreas but are uncompressed or less compressed when exiting the hollow bore of the needle. Optionally, wherein the second tines are also at any angle relative to the insertion direction of the insertion axis of the device, they may be compressed inside of the hollow bore of a needle and uncompressed or less compressed when exiting the hollow bore of a needle.

In still other aspects of the disclosure wherein a device is contemplated, the device may be a device comprising stimulators and/or sensors and may be described in detail in U.S. Pat. No. 6,542,776. Such a device may comprise for example four electrodes which may be placed in contact with the interior or the exterior wall of the gastrointestinal tract or the exterior of the pancreas. Optionally, such a device has electrodes supported by an electrode attachment member where the electrodes are in a plane with each other. One may envision four electrodes on a flat plate. Such an electrode attachment member may be attached to the gastrointestinal tract wall by sutures or staples. Optionally, the attachment member may have fixed tines at the point of placement of the attachment member to the wall of the gastrointestinal tract or the exterior of the pancreas. Such fixed tines may be inserted into the thickness of a gastrointestinal organ or the thickness of the pancreas in lieu of or in addition to sutures or staples in order to place the electrode attachment member. Optionally, the electrode attachment member further comprises an insertion axis extending through the electrode attachment member with a plurality of radially spaced arms as described above to place the electrode attachment member. Optionally, the electrode attachment member may be inserted to the body cavity or through the hollow bore of a needle. Optionally, the electrode attachment member may be constructed from a flexible material such as, e.g., silicone elsatomer or similar material. The base materials for the electrodes which may act as stimulators and/or sensors may be comprised of platinum, platinum-iridium alloys, titanium and the like. The electrodes may optionally be in an uncoated state or may be coated with materials such as iridium oxide or titanium nitride or the electrodes may be platinized or carbonized. Optionally, the electrode attachment member has a substantially circular configuration. Alternatively, the electrode attachment member may be in any suitable configuration such as for example, square, oval, rectangular, etc. Optionally, the electrodes may be distributed around the distal surface equidistantly from the center of the distal surface.

In certain aspects of the disclosure wherein a device is contemplated, the device may be that which is disclosed in U.S. Pat. No. 7,076,306 which is hereby incorporated by reference in its entirety. In certain aspects of the disclosure wherein a device is contemplated, the device may be a distributed microsystem setup in which an implanted microsystem is sutured or otherwise attached to the exterior of a gastrointestinal organ or the exterior of the pancreas. Such a device may be found in U.S. Pat. No. 7,720,539 which is hereby incorporated by reference. Optionally, such a device may incorporate a screw mechanism which may screw into the exterior of a gastrointestinal organ or the exterior of the pancreas. Such a device may be found in U.S. Pat. No. 7,711,437 which is hereby incorporated by reference. In certain aspects of the disclosure wherein a device is contemplated, the device may include an expandable member that fixes electrodes in contact with the gastrointestinal tract wall. Optionally such a device is radially expandable. Optionally such a device may be able to expand radially when passed through the hollow bore of a needle. Optionally such a device may be inserted into the thickness of the wall of the gastrointestinal tract. Such a device may be found in U.S. Pat. No. 7,676,270 which is hereby incorporated by reference. Other examples of electrical stimulation devices that may be used according to the present disclosure are found in U.S. Pat. Nos. 7,599,736, 7,477,994, 7,363,084, 7,310,557, 7,203,551, 7,177,693 and 7,016,735 which are hereby incorporated by reference. Other examples can be found in U.S. Pat. Pub. Nos. 20070049793 and 20050251219 which are hereby incorporated by reference.

In certain aspects of the disclosure wherein a plurality of radially extendable arms is contemplated, the arms may be affixed to the insertion axis of the device. Optionally, arms may be affixed via a hinge mechanism. Optionally, the arms may be affixed via flexible resilient wires to the insertion axis.

In certain aspects of the disclosure wherein placement of a device is contemplated, the methods may comprise a gastrointestinal wall tunneling instrument. Optionally, such an instrument may further comprise an elongate tubular member having proximal and distal ends and a lumen extending therethrough and an elongate expandable member located at the distal end of the tubular member. The expandable member may have proximal and distal ends wherein the proximal end of the expandable member is connected to the distal end of the tubular member. The expandable member may be everted, such that the distal end of the expandable member is positioned within the lumen of the tubular member. An example of this type of method and instrument can be found in WO/2009/009276 and is herein incorporated by reference.

Figure 6:
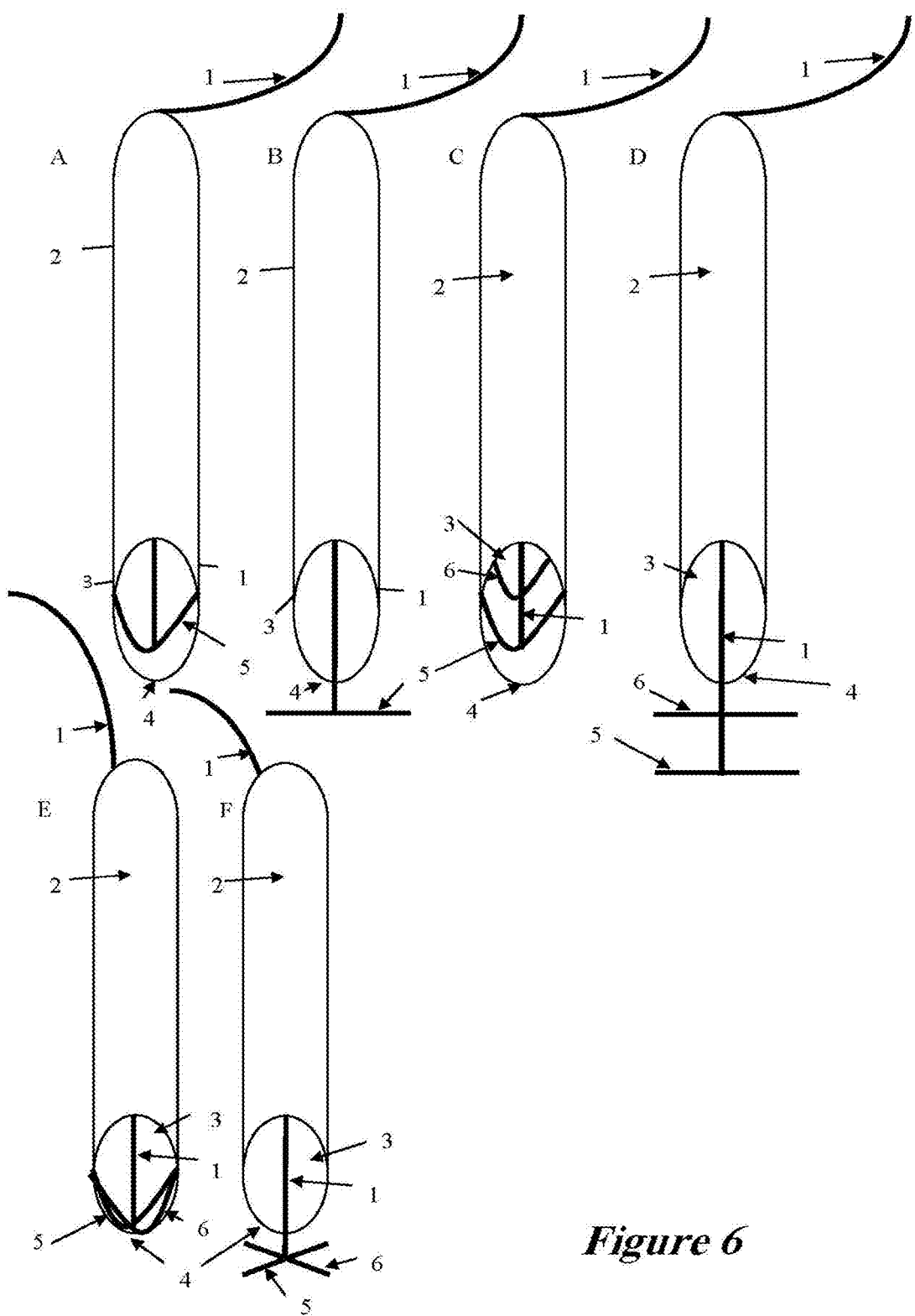
FIG. 6 A-F shows various electrode leads with radially spaced arms in various configurations inserted into and through the hollow bore of a needle.

Certain aspects of the disclosure may pertain to a method of placing a device and an implantable device as demonstrated in FIG. 6. Referring to FIG. 6A, an electrode lead with an insertion axis 1 is inserted into a needle 2 with a hollow bore 3. The needle has an entrance tip 4 which may be inserted through the skin and into or through the wall of the gastrointestinal tract. The electrode lead 1 may have a first or a single pair of radially spaced arms 5. Optionally, such arms 5 are in an angular position which is more acute than when passed through the needle as shown in FIG. 6A. Referring to FIG. 6B the radially spaced arms 5 are in an angular position which is less acute than or perpendicular to the electrode lead with an insertion axis 1 when passed through the needle. Referring to FIG. 6C the lead 1 may have a second or additional pair of radially spaced arms 6 at a distance from the first pair of radially spaced arms 5. Referring to FIG. 6C, each pair of radially spaced arms 5 and 6 may be retracted to an angle more acute than when passed through the needle 2. Referring to FIG. 6D, the first pair of radially spaced arms 5 and the second or additional pair of radially spaced arms 6 may be in an angular position which is less acute or perpendicular when passed through the hollow bore 3 of the needle 2. Optionally, referring to FIG. 6E the lead 1 may have a second or additional pair of radially spaced arms 6 in the same plane from the first pair of radially spaced arms 5. Referring to FIG. 6E, each pair of radially spaced arms 5 and 6 may be retracted to an angle more acute than when passed through the needle 2. Referring to FIG. 6F, the first pair of radially spaced arms 5 and the second or additional pair of radially spaced arms 6 may be in an angular position which is less acute or perpendicular when passed through the hollow bore 3 of the needle 2. It is also contemplated that a lead 1 may have a plurality of radially spaced arms in an odd numbered configuration, such as for example three arms instead of the first or single pair of radially spaced arms 5 or the second or additional pair of radially spaced arms as referenced throughout FIG. 6.

Figure 7:
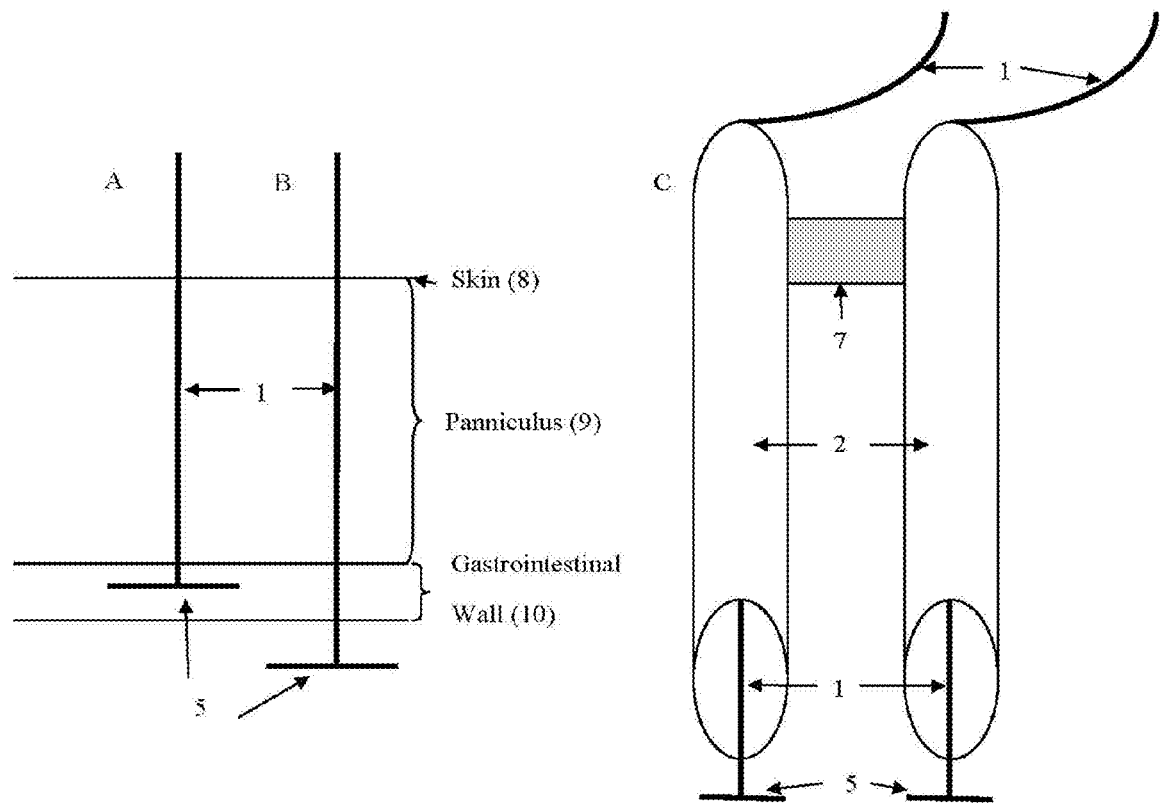
FIG. 7 A, B shows electrode leads with radially spaced arms inserted through the skin, panniculus and gastrointestinal wall after removal of insertion needles.

Certain aspects of the disclosure concern placement of a device as shown in FIGS. 7A and B. Referring first to FIGS. 6A and 6B, an electrode lead with an insertion axis 1 and radially spaced arms 5 may be inserted through a needle 2 comprising a hollow bore 3 wherein the entrance tip of the needle 4 may be inserted through the skin and into or through the gastrointestinal wall which may alternatively be considered the wall of the gastrointestinal tract. Referring to FIG. 7A, the needle 2 with the hollow bore 3 is removed after insertion of the electrode lead with an insertion axis 1 comprising radially spaced arms 5 such that the lead extends through the skin 8, the panniculus 9 and into the gastrointestinal wall 10. Alternatively, referring to FIG. 7B, the lead extends through the skin 8, the panniculus 9 and through the gastrointestinal wall 10.

Figure 8:
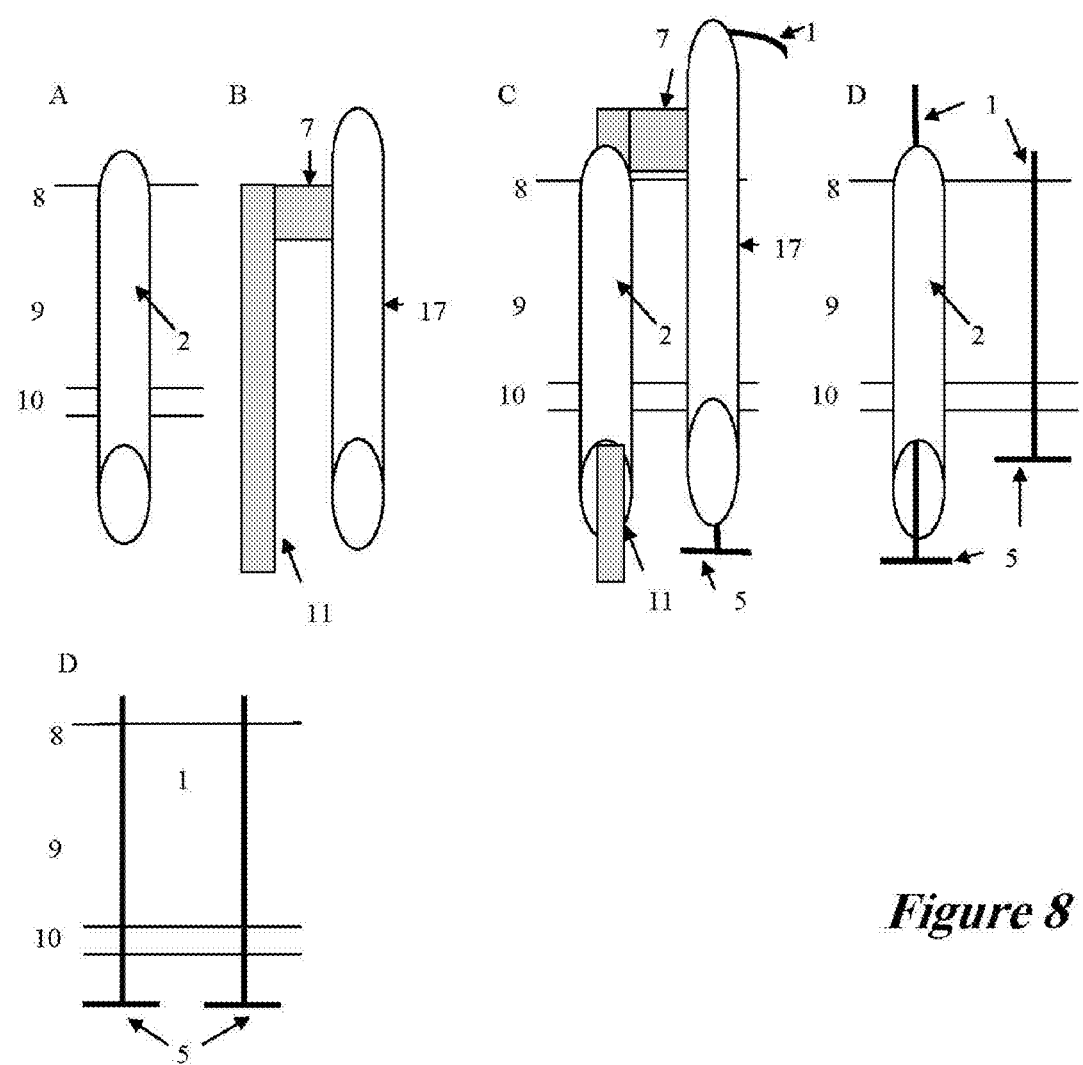
FIG. 8A-D shows methods and devices for using a needle with a guide rod for electrode leads with radially spaced arms.

Certain aspects of the disclosure pertain to optimal spacing of a plurality of electrodes in the wall of the gastrointestinal tract or through the gastrointestinal tract. Referring to FIG. 7C a plurality of needles 2 may be connected via a bridge 7 such that a plurality of electrode leads with insertion axis 1 comprising radially spaced arms 5 are spaced an optimal distance from each other. The bridge may be any length that achieves optimal spacing. Optionally, the bridge 7 may allow separation of the needles 2 by a distance of 1, 2, 3, 4, 5, 6, 7, 8, 9 or 10 mm or 1, 2, 3, 4, 5, 6, 7, 8, 9 or 10 cm or some distance therein. Alternatively, referring to FIG. 8A, a needle 2 may first be inserted through the skin 9, the panniculus 9 and either into or through the gastrointestinal wall 10. A second needle 17 as shown in FIG. 8B may include a bridge 7 connected to a guide rod 11. Referring to FIG. 8C, the guide rod 11 may be inserted into the needle 2 and an electrode lead with an insertion axis 1 comprising radially spaced arms 5 may be inserted into the second needle. The guide rod 11 is inserted through the first needle 2 as the second needle is inserted through the skin 8, the panniculus 9 and into or through the gastrointestinal wall 10. Referring to FIG. 8C, the second needle 17 may be removed leaving in place an electrode lead with an insertion axis 1 comprising radially spaced arms 5 which may be located in the gastrointestinal tract or in the gastrointestinal wall 10. Also referring to FIG. 8C, a second gastrointestinal lead with an insertion axis 1 and a plurality of radially spaced arms 5 may now be inserted in the first needle where the guide rod was previously located. Referring to FIG. 8D, the first needle may be removed so that there is more than one electrode lead with an insertion axis 1 and a plurality of radially spaced arms 5 extending through the skin 8, the panniculus 9 and into or through the gastrointestinal wall 10.

Figure 9:
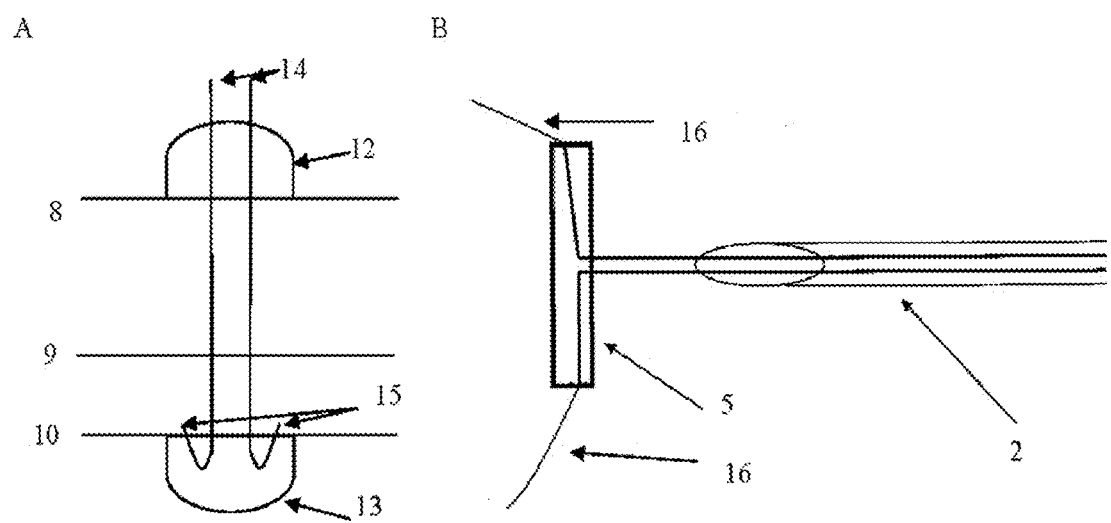
FIG. 9A shows a method of placing gastrointestinal leads with a percutaneous endoscopic gastronomy type device.
FIG. 9B shows conductive wire through an electrode lead with an insertion axis and a plurality of radially spaced arms.

Optionally, in certain aspects of the disclosure where placing of a device is concerned, the device may be a percutaneous endoscopic gastronomy type device. Referring to FIG. 9A, the device may comprise a skin bolster 12 attached or abutting the skin 8 and a gastric bolster 13 attached to or abutting the inside of the gastrointestinal wall 10. A plurality of electric leads 14 may be inserted through the skin bolster 12, through the panniculus 9 and through the gastrointestinal tract wall. The electric leads may be insulated and the lead ends 15 exposed and used as electrodes.

In certain aspects of the disclosure wherein an electrode lead with an insertion axis 1 comprising a plurality of radially spaced arms 5, the lead 1 and the arms 5 may be insulating a conductive wire 16 to serve as an electrode. Referring to FIG. 9B, an electrode lead with an insertion axis 1 comprising a plurality of radially spaced arms 5 which has been inserted through a needle 2 may have a conductive wire to serve as an electrode 16.

Certain aspects of the disclosure concern various means for maintaining the electrodes in position. Such other may include for example, anchors, sutures, anti-rotation mechanisms and device shape design.

In certain aspects of the disclosure wherein a device is concerned, the device may be constructed of a size and shape such that it can be deployed through the mouth and esophagus with the aid of an endoscope. Optionally, the stimulator is of a generally small profile when delivered to the implant site.

Still further, the implant be constructed and/or implanted so that the device predictably maintains electrical contact with a muscle layer of the gastrointestinal tract wall. Optionally, the device may be constructed of a configuration or shape that prevents device rotation, or may be constructed so that device rotation or movement does not interfere with the electrode/muscle layer contact. Such a device may be found in WO/2002/089655 which is hereby incorporated by reference.

In certain aspects of the disclosure wherein placing a device is concerned, such methods may include a means for maintaining the device in proper orientation so that the electrodes, sensors or other transducers on the device maintain contact with a preferred area or layer of the gastrointestinal tract wall, for example, so that the electrodes, sensors or other transducers are preferentially facing a desired wall of the gastrointestinal tract within a submucosal space. An anti-rotation means may be provided that prevents rotation of the implant around axes that would move electrodes, sensors or transducers away from intimate contact with a desired area of the gastrointestinal wall, such as, e.g., a muscle layer or mucosal layer.

In certain aspects of the disclosure wherein placing a device is concerned, the shape of the device may, for example, have a broad aspect when viewing that side of the device intended to be in contact with a particular layer of the gastrointestinal tract wall (e.g., a muscle layer or mucosal layer); i.e., the top-view of the device has relatively large length and width dimensions with respect to the height dimension of the device given by its side-views. Optionally, the aspect ratio of the device, defined as the width of a side-view divided by the height of the device is larger than about 1, preferably larger than about 1.4 and more preferably larger than about 1.8.

In certain aspects of the disclosure wherein placing a device is concerned, an anti-rotation means may be provided that prevents rotation of the device about an axis parallel to an intended tissue plane of contact. A device in one variation is dimensioned so that the aspect ratio of the device viewed along an axis parallel to the intended plane of contact is greater than one and preferably greater than 1.4 and more preferably greater than 1.8.

The aspect ratio as used herein may be the width to height ratio of the aspect viewed along a particular axis. Alternatively, the anti-rotation device may comprise an extendible or expandable portion or member that extends into a position that prevents rotation of the electrodes away from contact with the muscle layer of the gastrointestinal tract wall.

In certain aspects of the disclosure wherein placing a device is concerned, an anti-rotation means may be provided that prevents rotation of the device about an axis parallel to a common plane on which the electrodes may lie. Accordingly, a device may be dimensioned so that the aspect ratio of the device viewed along an axis parallel to plane on which the electrodes may lie is greater than one and preferably greater than 1.4 and more preferably greater than 1.8. The device in this instance may be defined by a plane on which the electrodes lie.

In certain aspects of the disclosure wherein placing a device is concerned, the device may have a relatively small profile when placed through the wall or into the wall of the gastrointestinal tract and may be altered to have a different shape when implanted, to prevent rotation and/or provide optimal sensor/transducer/electrode contact with the gastrointestinal tract wall.

In certain aspects of the disclosure wherein the device is contemplated, the device may be designed to promote encapsulation or tissue ingrowth, e.g. by choice of material, coatings or surface texture. Optionally an electrode(s) or sensor(s) or surrounding area may be coated with a material such as P-15, which is a commercially available compound that promotes cellular adhesion and tissue ingrowth.

In certain aspects of the disclosure wherein the device is contemplated, the device or portions of the device may be constructed of or coated with substances that inhibit tissue ingrowth.

EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Example 1

Figure 2A:
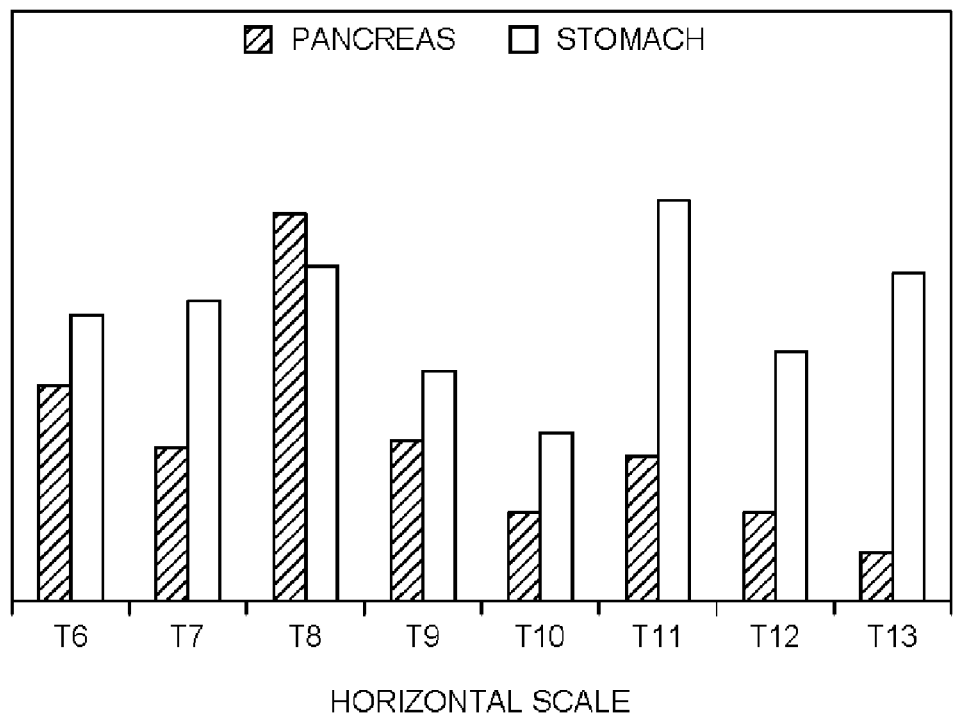
FIG. 2A shows the percentage of pancreatic (red) and gastric (green) DRG neurons that are double labeled at various spinal segments.
Figure 2B:
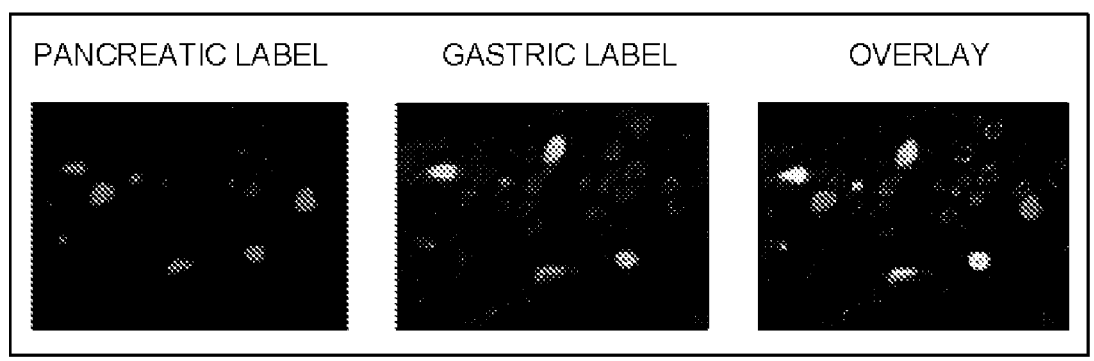
FIG. 2B is a representative photomicrograph of several double labeled neurons in a DRG section.

Based on the hypothesis that irritation of the stomach could affect the pancreas, the neural convergence in the two neighboring organs, specifically focused on dichotomizing branches of afferent neurons, was examined. A subset of afferent neurons innervates both the stomach and the pancreas via dichotomous peripheral branches. This was examined by injection of two distinct retrogradely transported neuronal dyes into the pancreas CTB-594 (cholera toxin subunit B [CTB] 594 ["red"]; Invitrogen; 24 µl in 12 sites, 2 µl/site at a concentration of 2 µg/ul) and in the stomach (CTB-488 ["green"] at the same concentration using the same injection strategy injecting it into the muscle wall and under the serosa) of rats. Five days later, the animals were euthanized and the DRGs from thoracic T6-13 segments were harvested and sectioned. The percentage of single and double labeled neurons were counted. FIG. 2A shows the number of double labeled cells expressed as a percentage of the total number of gastric- and pancreatic-labeled cells. Of 2333 DRG neurons examined, we found 1779 originating from the stomach, 898 originating from the pancreas and 344 from both. Thus, overall about 19% of all pancreatic cells also expressed gastric labeling while 38% all gastric cells also expressed pancreatic labeling. However, these numbers don't tell the whole story: in T8 for instance more than half of all pancreatic segments also received innervation from the stomach; similarly, in T10 more than 50% of all gastric neurons also innervated the pancreas. For the rest of this discussion, we have used the term "gastropancreatic nerve" for nerves that receive input from both the stomach and pancreas. A representative photomicrograph of double labeling is shown in FIG. 2B.

Figure 3:
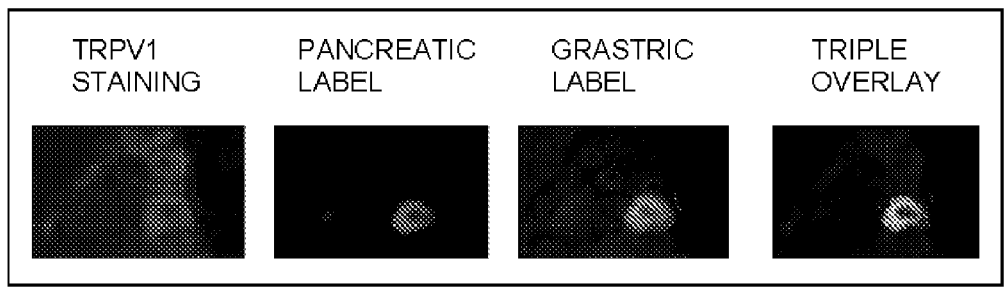
FIG. 3 illustrates an example of an TRPV1 staining in gastropancreatic neuron.

As shown in Table 1, most gastropancreatic nerves expressed markers for nociceptive neurons that in equal if not higher frequency than single labeled nerves. Nociceptor neurons are considered either peptidergic or non-peptidergic in origin. CGRP is a commonly used marker for the former and IB4 for the latter (however, there is considerable overlap as can be seen from the numbers). Both TRPV1 and P2X3 (a purinergic G-protein coupled receptor) are highly characteristic of nociceptors and are very important molecules in transducing tissue injury into electric signals. An example of an TRPV1 staining in gastropancreatic neuron is shown in FIG. 3.

TABLE 1

|  | Pancreas | Stomach | Both |
|---|---|---|---|
| CGRP | 68% | 79% | 85% |
| IB4 | 59% | 50% | 67% |
| P2X3 | 42% | 56% | 64% |
| TRPV1 | 73% | 78% | 71% |

Example 2

Activation of Gastropancreatic Neural Reflexes Induce Pancreatic Injury

Figure 4:
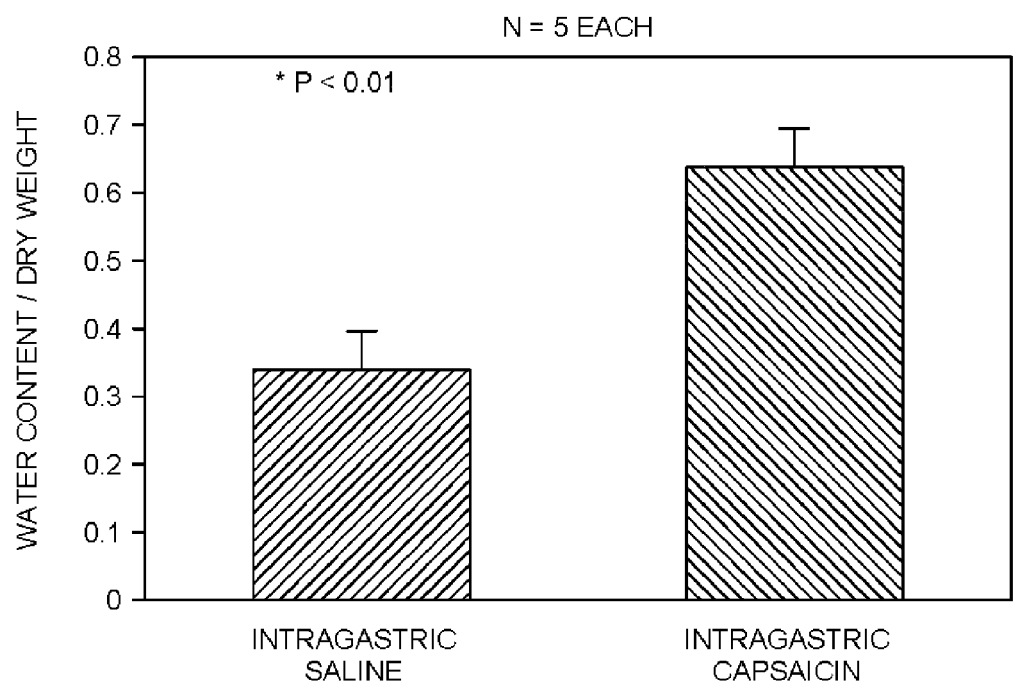
FIG. 4 shows that intragastric capsaicin causes pancreatic edema.

Next the functional correlate of this anatomical convergence was determined. It was hypothesized that intragastric capsaicin will activate TRPV1 on gastric branches of dichotomous gastropancreatic nerves and via an axonal reflex result in edema of the pancreas. After pyloric ligaton, intragastric infusion of 1.2 ml of 1.6 µM capsaicin was followed 30 minutes later by harvesting of the pancreas and measurement of water content. The results (FIG. 4) show that intragastric capsaicin causes pancreatic edema, strongly supporting the hypothesis of gastropancreatic axonal reflexes.

Example 3

Figure 5:
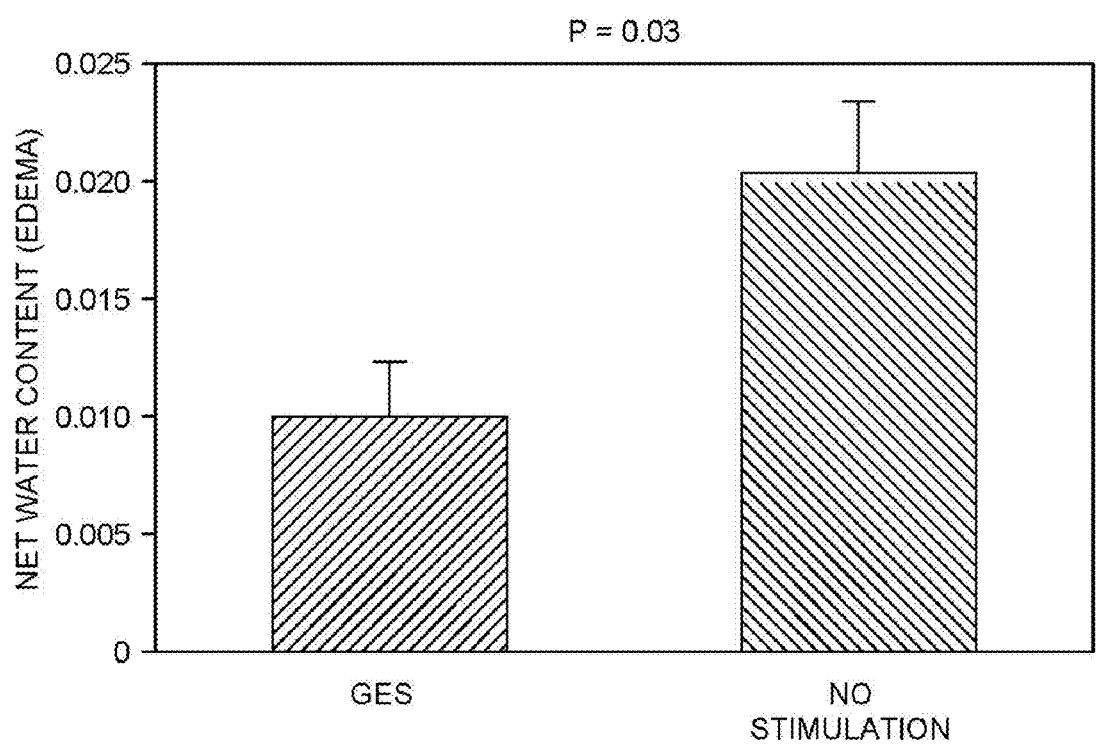
FIG. 5 shows net water content in the pancreas (edema) 24 h after cerulean injections with and without GES.

Gastric Electrostimulation (GES) was performed in rats injected with creulein using a pair of electrodes. Creulein is a decapeptide with hypotensive activity that stimulates smooth muscles and increases digestive secretions. It is similar to cholecystokinin and the gastrins, but much more potent as a stimulant to gallbladder contraction and also stimulates release of insulin. A control group of rats had electrodes implanted but were not stimulated. Electrical stimulation was begun at the time of injection and continued for 6 hours. Electrical stimulation was administered in repetitive trains of pulses set on for a range of period between about 0.1 seconds to less than or equal to 5 seconds and set off for a range of period between about 0 to less than or equal to 10 minutes. Further, the repetitive trains of pulses were administered in the range between about IHz. to less than or equal to 150 Hz, a pulse width in the range between about 0.1 ms to less than or equal to 2.0 ms, and an amplitude in the range between about 0.1 mA to less than or equal to 20.0 mA. Twenty four hours after the first injection, rats were sacrificed and pancreas harvested. As can be seen from FIG. 5, gastric electrical stimulation resulted in 50% less edema in the pancreas as compared to the controls.

Although preferred embodiments have been depicted and described in detail herein, it will be apparent to those skilled in the relevant art that various modifications, additions, substitutions and the like can be made without departing from the spirit of the disclosure and these are therefore considered to be within the scope of the disclosure as defined in the claims which follow. All patents and publications mentioned herein are hereby incorporated by reference as if reproduced in their entirety.

References

The following references, to the extent that they provide exemplary procedural or other details supplementary to those set forth herein, are specifically incorporated herein by reference.

U.S. Pat. No. 5,292,344
U.S. Pat. No. 5,423,872
U.S. Pat. No. 5,690,691
U.S. Pat. No. 5,836,994
U.S. Pat. No. 6,542,776
U.S. Pat. No. 7,016,735
U.S. Pat. No. 7,076,306
U.S. Pat. No. 7,177,693
U.S. Pat. No. 7,203,551
U.S. Pat. No. 7,310,557
U.S. Pat. No. 7,363,084
U.S. Pat. No. 7,477,994
U.S. Pat. No. 7,599,736
U.S. Pat. No. 7,676,270
U.S. Pat. No. 7,711,437
U.S. Pat. No. 7,720,539
U.S. Pat. Pub. No. 20050251219
U.S. Pat. Pub. No. 20070049793
WO1999/30776
WO2001/076690
WO2002/089655
WO2009/009276
Abo et al., *Dig. Dis. Sci.*, 45:129-135, 2000.
Bellahsene, et al., *Am. J. Physiol.*, 262:G826-G834, 1992.
Baron et al., *New England J. of Medicine*, 340:1412-1417, 1999.
Chen et al., *J. Gastro. Hepato.*, 13(Suppl.):5232-5236, 1998.
Chen et al., IEEE-EMBC and CMBEC, Theme 7: Instrumentation, pp. 1691-1692, 1995.
Duggan, J P and D A Booth, *Science*, 231:609-611, 1986.
Eagon, J C and K A Kelly, *Am. J. Physiol.*, 265:G767-G774, 1993.
Hocking et al., *Gastroenterol.*, 103:1811-1816, 1992.
Lin et al., *Am. J. Physiol.*, 274(1 Pt 1):G186-191, 1998.
Lin et al., *Dig. Dis. Sci.*, 45:652-656, 2000.
McCallum et al., *Gastroenterol.*, 114:456-461, 1998.
Miedema et al., Surg 111:143-150, 1992.
Mintchev et al., *Gut*, 43:607-611, 1998.
Mintchev et al., *Journal of Medical Engineering & Technology*, 23:5-9, 1999.
Mintchev et al., *Gastroenterology*, 118:258-263, 2000.
Norton, et al., *Drugs*, 61: 1581-1591, 2001.
Phillips, R J and T L Powley, *Am. J. Physiol.* 271:R766-R779, 1996.
Qian, L W, et al., *Am. J. Physiol.* (*Gastrointest. Liver. Physiol.* 39) 276:G387-392, 1999.
Steer et al., *New England J. of Medicine*, 332:1482-1490, 1995.
Wright et al., *Gastroenterology*, 84:747-751 (1983).
Yoshinaga, et al., *Japanese J. Pharmacol*, 8444-50, 2000.
Zapater, et al., *Clin. Drug Invest.*, 20:401-408, 2000.
Zhang et al., *Current treatments of Gastroenterol.* 9:351-360, 2006.

What is claimed is:

1. A method of preventing acute pancreatitis in a subject comprising: positioning stimulatory electrodes in the stomach of the subject and administering repetitive pulse trains of gastric electrical stimulation that are on for 0.1 seconds to 5 seconds and off for up to 10 minutes and are effective for suppressing the inflammatory response in the pancreas.

2. The method of claim 1, wherein said subject has or is undergoing an endoscopic procedure.

3. The method of claim 2, wherein said endoscopic procedure is selected from the group consisting of Endoscopic retrograde cholangiopancreatography (ERCP), and endoscopic sphincterotomy.

4. The method of claim 2, wherein said electrical stimulation is administered concurrently with an endoscopic procedure.

5. The method of claim 2, wherein said electrical stimulation is administered following an endoscopic procedure.

6. The method of claim 1, wherein said repetitive pulse trains are administered in the range of about 1 Hz to 150 Hz.

7. The method of claim 1, wherein said repetitive pulse trains have a pulse width in the range of about 0.1 ms to 2.0 ms.

8. The method of claim 1, wherein said repetitive pulse trains have an amplitude in the range of about 0.1 mA to 20.0 mA.

9. The method of claim 1, wherein said electrodes are placed by laproscopic, endoscopic or surgical means.

10. The method of claim 1, wherein said repetitive trains of pulses have a pulse width in the range of about 1 ms to 2 ms.

11. A method of preventing acute pancreatitis in a subject comprising: positioning a stimulatory electrode in the peritoneal cavity, in proximity of a dichotomously branched spinal nerve innervating the stomach and the pancreas and administering repetitive pulse trains of electrical stimulation where the pulses trains are on for 0.1 to 5 seconds and off for up to 10 minutes, and are effective for suppressing the proinflammatory spinal reflexes.

12. The method of claim 11, wherein said repetitive pulse trains are administered in the range of about 1 Hz to 150 Hz.

13. The method of claim 11, wherein said repetitive pulse trains have a pulse width in the range of about 0.1 ms to 2.0 ms.

14. The method of claim 11, wherein said repetitive pulse trains have an amplitude in the range of about 0.1 mA to 20.0 mA.

15. The method of claim 11, wherein said electrodes are placed by laproscopic, endoscopic or surgical means.

16. The method of claim 11, wherein said stimulatory electrodes are placed in the stomach, small intestines, colon or anorectum.

17. The method of claim 11, wherein said repetitive trains of pulses have a pulse width in the range of about 1 ms to 2 ms.

* * * * *